(12) United States Patent
Choi et al.

(10) Patent No.: US 8,913,119 B2
(45) Date of Patent: Dec. 16, 2014

(54) SHORT DISTANCE IRIS RECOGNITION CAMERA

(75) Inventors: Kyung Yong Choi, Seoul (KR); Deok Yong Ko, Seoul (KR)

(73) Assignee: ARIA Hightech Co., Ltd., Seoul (KR)

( * ) Notice: Subject to any disclaimer, the term of this patent is extended or adjusted under 35 U.S.C. 154(b) by 0 days.

(21) Appl. No.: 13/816,444

(22) PCT Filed: Jul. 22, 2011

(86) PCT No.: PCT/KR2011/005420
§ 371 (c)(1),
(2), (4) Date: Feb. 11, 2013

(87) PCT Pub. No.: WO2012/020931
PCT Pub. Date: Feb. 16, 2012

(65) Prior Publication Data
US 2013/0135513 A1  May 30, 2013

(30) Foreign Application Priority Data

Aug. 13, 2010  (KR) ........................ 10-2010-0078277

(51) Int. Cl.
| | |
|---|---|
| *H04N 7/18* | (2006.01) |
| *H04N 5/232* | (2006.01) |
| *H04N 9/00* | (2006.01) |
| *H04N 5/225* | (2006.01) |
| *G06K 9/20* | (2006.01) |
| *A61B 5/00* | (2006.01) |
| *A61B 3/14* | (2006.01) |
| *G06K 9/00* | (2006.01) |
| *A61B 5/117* | (2006.01) |

(52) U.S. Cl.
CPC ............ *H04N 5/2254* (2013.01); *G06K 9/2027* (2013.01); *A61B 5/0077* (2013.01); *A61B 3/14* (2013.01); *H04N 5/2256* (2013.01); *A61B 5/6821* (2013.01); *G06K 9/209* (2013.01); *G06K 9/2036* (2013.01); *G06K 9/00604* (2013.01); *A61B 5/117* (2013.01)
USPC .............................. 348/78; 348/345; 382/117

(58) Field of Classification Search
CPC .... A61B 3/113; A61B 3/145; G06K 9/00604; G06K 9/00597; G06K 9/0061; H04N 5/23219; G06T 2207/30216; G06T 7/408
USPC ..................... 348/78; 382/117, 115
See application file for complete search history.

(56) References Cited

U.S. PATENT DOCUMENTS 7,271,839 B2 * 9/2007 Lee et al. ..................... 348/346
7,280,678 B2 * 10/2007 Haven et al. ................. 382/117
(Continued)

FOREIGN PATENT DOCUMENTS

| JP | 06-000163 | 1/1994 |
| JP | 2004-164483 | 6/2004 |
| KR | 10-2005-0043097 | 5/2005 |

*Primary Examiner* — Daniel M Pasiewicz
*Assistant Examiner* — Selam Gebriel
(74) *Attorney, Agent, or Firm* — Jordan and Hamburg LLP

(57) ABSTRACT

The short distance iris recognition camera of the present invention has a prism, installed on top of a guide for an infrared LED light, which has an inclined surface and a protrusion part, thereby enhancing the degree of uniformity in brightness around an iris, and thus enhancing iris recognition, and also effectively preventing static electricity from being delivered to internal devices. To accomplish this, the camera for iris recognition according to the present invention comprises a sensor and accessory circuits, a lens, and a lighting source including a white light and an infrared LED light. The lighting source is spaced apart from the lens centerline by a set length. The object plane of the lens is located where the iris is located, and is spaced apart by a set length L from the end of the lens. In practice, the object plane comprises the area around the lens centerline. The phase surface of the lens is an image sensor surface. The lighting source is disposed exactly or nearly parallel to the lens centerline such that the lighting centerline directs the object plane of the lens and has a lighting inclination angle of at least the arctangent of D/L with respect to the centerline of the lens. And also, the lighting centerline is separated from the centerline of the lens and inclined with respect to the object plane.

7 Claims, 10 Drawing Sheets

(56) References Cited

U.S. PATENT DOCUMENTS

2005/0264758 A1\* 12/2005 Wakamori ................... 351/206
2009/0016574 A1\* 1/2009 Tsukahara ................... 382/117

\* cited by examiner $$\frac{\sin i}{\sin r} = \frac{v1}{v2} = n12$$

| conventional example | example of present invention |
| --- | --- |
| maximum value/minimum value of relative brightness = 7.98/5.27 = 1.51 | maximum value/minimum value of relative brightness = 6.77/5.60 = 1.21 |

SHORT DISTANCE IRIS RECOGNITION CAMERA

TECHNICAL FIELD

The present invention relates to an iris recognition camera and, more particularly, to a short distance iris recognition camera which allows a prism having an inclined surface and a protrusion part to be installed in the upper portion of a guide for a lighting IR LED (infrared LED), thereby enabling a lighting direction and an irradiation range to be designed as desired, which improves the uniformity of brightness around the iris, thereby improving the efficiency of iris recognition, which effectively prevents static electricity from being transferred to internal devices through the IR LED, and which provides visual or aural notification that iris recognition is being performed, thereby enhancing the efficiency of iris recognition.

BACKGROUND ART

As is known, certificates are being widely used in almost all fields of electronic commerce (e-commerce), not only in Internet shopping but also in online banking, mobile stock trading, and the Internet issuance of public documents.

Such certificates are online forms of identification that are necessary to validate a person's identity so as to allow him or her to conduct convenient Internet transactions, but they are vulnerable in terms of security because certificate files and passwords may be obtained through hacking.

Furthermore, since conventional methods have a problem with the validation of identities, a scheme using bio information is being pursued. Biometric technology has attracted attention as user authentication technology that provides convenience and safety. It was selected as one of the "10 promising technologies for the 21st century" by U.S. MIT, Gartner Group.

With regard to biometric technology, iris recognition technology is the most secure technology among currently implemented biometric technologies, since the probability of one human iris having the same pattern as another is approximately one in six billion. Furthermore, currently, in the U.S., Japan, Great Britain and Germany, identification based on iris recognition is being used as identification means.

In general, a lighting IR LED (infrared LED) is used for iris recognition. The radiation angle (lighting angle) of the lighting IR LED is determined to be twice an angle that is a half of the maximum value of emitted light.

An example of such a radiation angle is as illustrated in FIG. 10. In this case, the radiation angle (lighting angle) is about 125 degrees.

Furthermore, an iris recognition camera lens has a specific field of vision or field of view, and an image within the angular range may be formed on a sensor. It is represented using angles in terms of the specification.

The field of view of a lens may have a variety of combinations depending on the distance between the lens and the iris, the resolution (or the number of pixels) of an image sensor that validates an identity based on an iris image, the performance of a device that is used to validate an identity based on an image, and the structure of a program that is used to perform processing.

For example, when the distance between a lens and an eye is set to a short distance of 5 to 15 cm and an identity is validated based on an iris image using a typical signal processing device having a speed of hundreds of MHz, it is determined that it is sufficient if an image sensor has a resolution of about 640×480 pixels.

In this case, the field of view of the lens is preferably about two or three times the size of the pupil, and about 15 degrees are appropriate.

The range of lighting is preferably wider than the field of view of the lens, in which case the uniformity of the brightness of lighting should be at a level at which image quality that enables an iris image to be desirably processed can be guaranteed. That is, at least 70~80% is preferable.

The uniformity of brightness may be determined using various methods. In accordance with the simplest of these methods, the relative uniformities of brightness may be compared based an the brightness_maximum value/the brightness_minimum value.

Furthermore, to achieve effective lighting, it is preferred that a lighting range be somewhat wider than the field of view of a lens, that is, by 20~50%.

That is, when a lighting range is excessively narrow, a variety of additional means are required to achieve the uniformity of brightness in light of the radiation characteristics of a lighting IR LED. In contrast, when a lighting range is wide, relatively strong lighting is required, and thus there arise the disadvantage of power consumption increasing and the disadvantage of the number of lighting components increasing. Since the brightness of lighting is inversely proportional to the square of a lighting area, an amount of light four times the initial amount of light is required to achieve the same brightness when a lighting range is doubled.

As illustrated in FIG. 7, when a lighting IR LED 2 is vertically disposed within a guide 3, a large amount of light is required because a radiation angle (lighting angle) should be widened to irradiate an area around the iris with an appropriate amount of light so as to capture the iris of an eye that is located away from the lens 1 by a specific distance, with the result that the power consumed by the lighting IR LED 2 increases.

Additionally, there are the disadvantage of the lighting IR LED 2 functioning as a conductor that transmits external static electricity to internal mechanical devices (not shown), and the disadvantage of the uniformity of brightness around the iris being deteriorated when the lighting IR LED 2 is used or short-distance lighting.

When a lighting IR LED 2 is inclined and then disposed in a guide as illustrated in FIGS. 8 and 9, there are disadvantages in that an additional support (not shown) is required to, upon installing the lighting IR LED 2 in the guide 3, determine an arbitrary radiation angle (lighting angle) and keep the angle constant, in that there is difficulty with assembly, and in that quality control is extremely difficult upon mass production because it is not easy to determine a predetermined angle with an unaided eye after assembly has been finished.

In addition, since the lighting IR LED 2 is inclined and then disposed within the guide 3, an unnecessary space is formed in the hole of the guide 3 that guides the lighting IR LED 2, thereby causing the disadvantage of supporting force being weakened, the appearance thereof being undesirable, and the size thereof increasing.

Furthermore, in this method of inclining and disposing the lighting IR LED 2, the lighting IR LED 2 is exposed directly to the outside in the same manner as shown in FIG. 7, and thus there are the disadvantage of being weak to external static electricity and the disadvantage of the uniformity of brightness around the iris being poor.

While the scheme of FIG. 9 can improve the uniformity of brightness around the iris using a prism 4 with planar top and bottom surfaces, compared to the scheme of FIG. 8, it still has the disadvantages of the scheme of FIG. 8.

Since the lighting IR LED 2 consumes a specific amount of power to achieve a predetermined light output and thus generates heat upon operation, it is disposed in the metallic guide 3 in order to achieve heat dissipation effects.

In this case, static electricity of thousands of volts is discharged from a human body or air via the metallic guide 3 and internal circuits, and thus erroneous operation of the circuits may occur.

Therefore, a static electricity absorption element is generally used as a static electricity prevention means. The use of the static electricity absorption element is a factor resulting in an increase in cost. Furthermore, since some countermeasure other than a simple static electricity absorption element is required as the prevention means, there is a disadvantage in that the configuration of a camera module that is used to capture the iris is complicated.

DISCLOSURE

Technical Problem

Accordingly, the present invention was developed to overcome the disadvantages of the conventional iris recognition camera, and an object of the present invention is to provide an iris recognition camera that can improve the uniformity of brightness around the iris without changing the state of a lighting IR LED being installed and that can also prevent static electricity from being discharged to internal circuits.

Technical Solution

In order to accomplish the above object, there is provided a short distance iris recognition camera comprising a sensor and appendant circuits, a lens, and a lighting source including a white light source and a lighting IR LED, the lighting source is spaced apart from a lens center line of the lens by a predetermined distance, an object plane of the lens is a location at which an iris is placed is spaced apart from an end of the lens by a predetermined distance L, and is actually a region around the lens center line, an imaging surface of the lens is an image sensor surface, and wherein a lighting center line is formed to have an inclined lighting angle corresponding to arctangent D/L with the lens center line of the lens to be oriented to the object plane of the lens.

Here, the lighting source is disposed in parallel with or approximately in parallel with the lens center line of the lens, and a prism is disposed to be spaced apart from the lens center line of the lens and to irradiate the object plane in an inclined manner.

The incident surface of the prism may be configured as an inclined surface so as to irradiate the object plane with respect to the vertical disposition of the lighting IR LED.

Minute protrusions may be formed on both or one of the incident and exit surfaces of the prism to disperse light and thus make brightness uniform.

Furthermore, the exit surface of the prism may be configured as a convex spherical surface or a concave spherical surface, thereby easily adjusting lighting to an arbitrary angle.

Advantageous Effects

The present invention has the effects of simplifying a structure by optimizing a required field of view, minimizing power consumption, providing effective lighting means capable of remarkably improving the uniformity of lighting brightness, preventing erroneous operation regardless of static electricity of thousands of volts that may be externally generated, and increasing a user's convenience by providing notification of a location at which the iris can be accurately captured.

Furthermore, the present invention achieves the effect of reducing the size of an iris capturing camera so that it has very small dimensions of about a few square centimeters.

The present invention provides a high-performance iris recognition system that can be sold to consumers at a relatively low price, thereby achieving the effect of enhancing consumers' social and economic security using biometric recognition.

BEST MODE

The short distance iris recognition camera of the present invention will be described in detail with reference to the accompanying drawings, that is, FIGS. 1 to 6.

Figure 1:
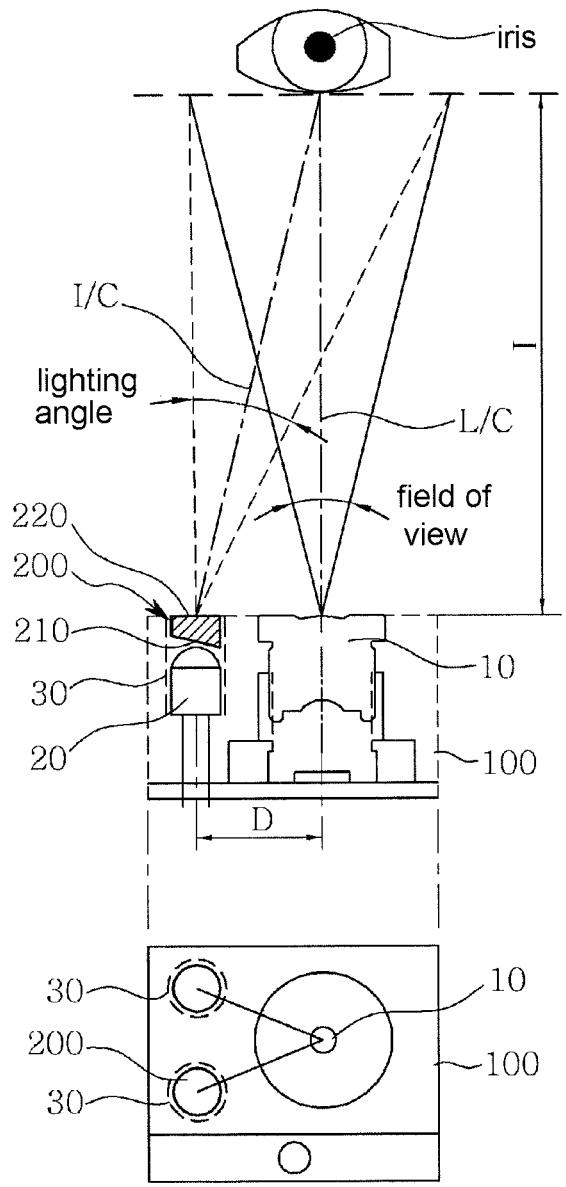
FIG. 1 shows plan and front views of the present invention, and schematic diagrams illustrating the lighting center line and lighting angle of lighting that is shed on the iris of an eye.

As illustrated in FIG. 1, the iris capturing camera includes a sensor (not shown) and appendant circuits (not shown), a lens 10, indication light 300, and a lighting source 20 including a white light source and a lighting IR LED.

The indication light 300 provides guidance so that a user's iris is placed exactly on the object plane of the lens. Although the indication light 300 visually notifies the user that iris recognition is being performed, notification may be aurally provided using a sound device, or both the indication light 300 and the sound device may be used together.

The lighting source 20 is spaced apart from the lens center line L/O of the lens 10 by a predetermined distance D.

The object plane of the lens 10 is a location at which the iris is placed, is spaced apart from the end of the lens 10 by a predetermined distance L, and is actually an area around the lens center line L/C. The imaging surface of the lens is an image sensor surface.

A lighting center line I/C has an inclined lighting angle of an arctangent D/L with respect to the lens center line L/C of the lens so that the lighting center line I/C is directed toward the object plane of the lens 10.

Here, the lighting source 20 is disposed in parallel with or approximately in parallel with the lens center line L/C of the lens 10, and is spaced apart from the lens center line L/C of the lens 1. A prism 200 is installed with the lighting IR LED 20 covered with a guide 30 so that oblique lighting is shed on the object plane.

The incident surface 210 of the prism 200 is formed as an inclined surface so that the object plane is illuminated with respect to the vertical disposition of the lighting IR LED 20, and thus the uniformity of brightness around the iris is improved regardless of a small amount of light, with the result that the iris can be recognized within a short distance, preferably within the range of 3 to 20 cm.

In addition, since it is preferable in terms of appearance that the exit surface 220 of the prism 200 be formed on the same plane as the top surface of the casing 100 of the camera module, the exit surface 220 of the prism 200 is formed on the plane.

Figure 2:
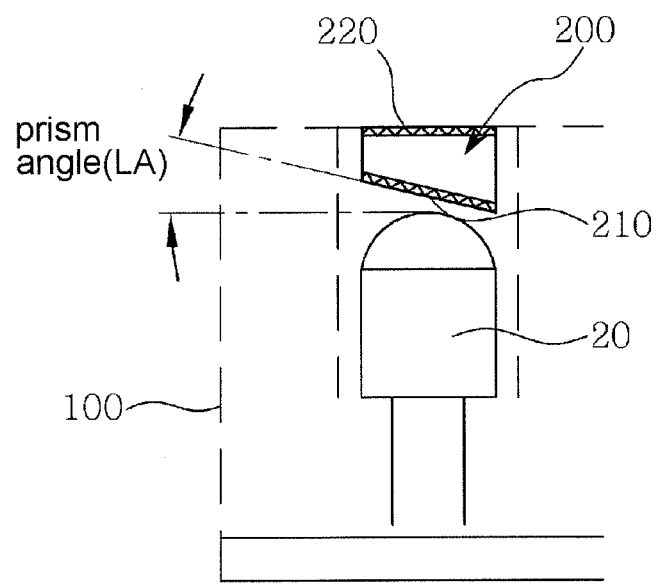
FIG. 2 is a partial enlarged view of FIG. 1.
Figure 3:
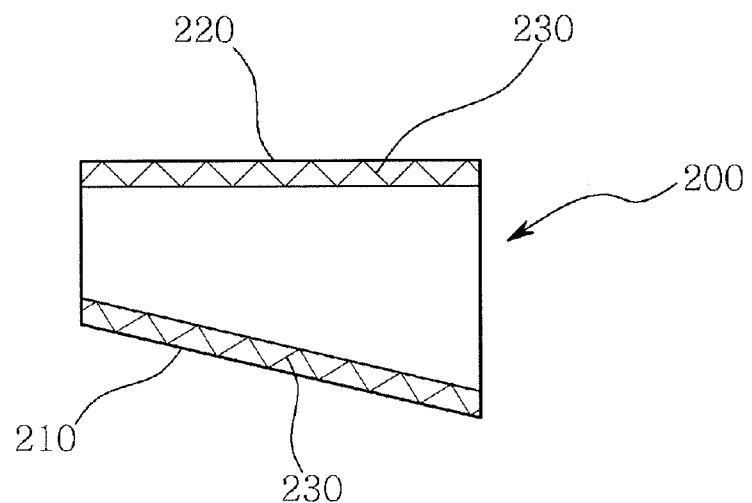
FIG. 3 is a partial enlarged view of the prism of FIG. 2.

As illustrated in FIGS. 2 and 3, it is preferable to form minute protrusions 230 on both or one of the incident and exit surfaces 210 and 220 of the prism 200 so as to scatter light and thus make brightness uniform.

Figure 4:
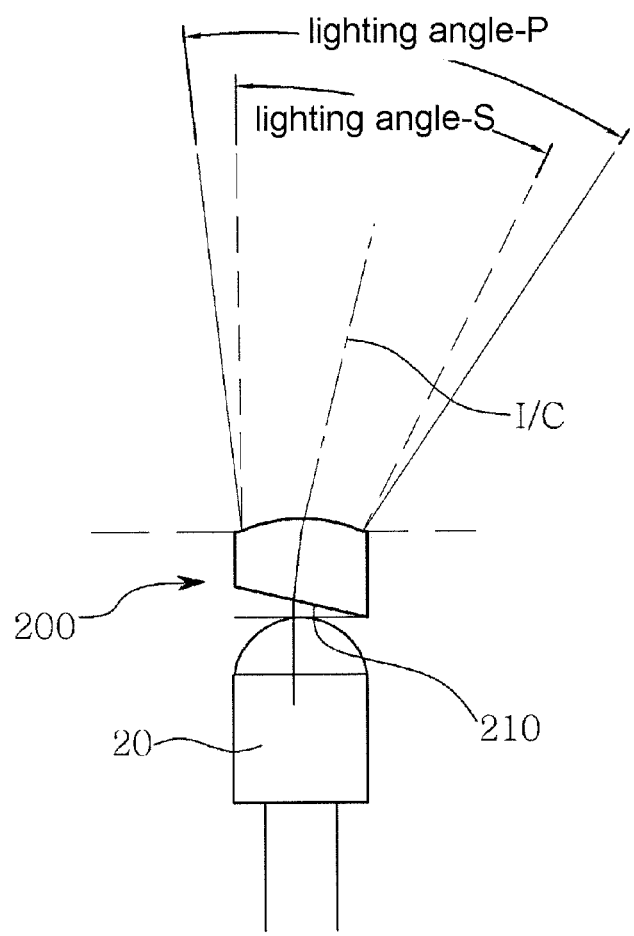
FIG. 4 is a schematic diagram showing a lighting angle when a prism whose exit surface is configured as a convex spherical surface is used.
Figure 5:
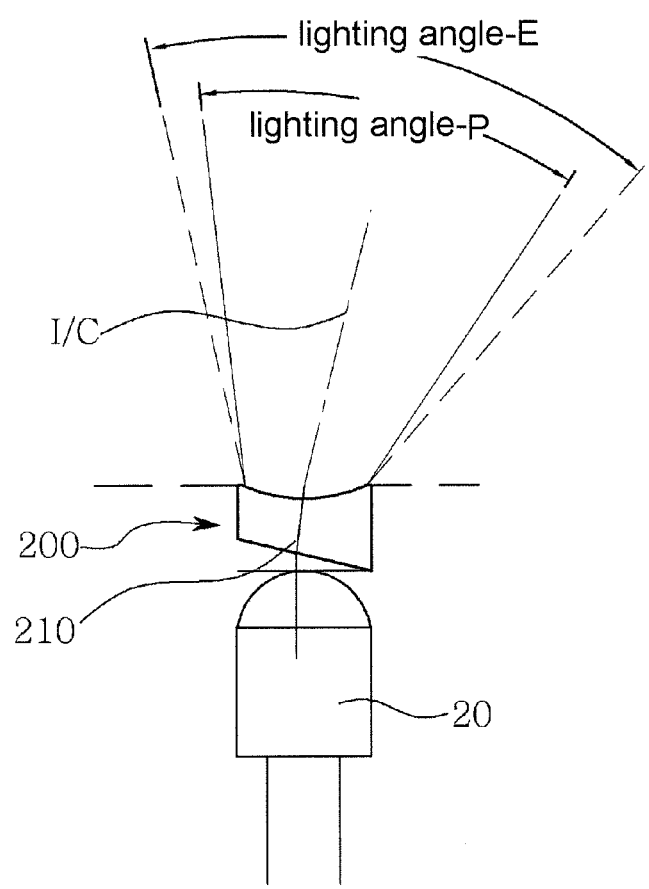
FIG. 5 is a schematic diagram showing a lighting angle when a prism whose exit surface is configured as a concave spherical surface is used.

Meanwhile, the lighting angle of the lighting IR LED 200 is fixed to one of several angles, for example, 15 degrees, 30 degrees, and 50 degrees, upon manufacturing. Here, when a different lighting angle is necessary, lighting may be performed at an arbitrary angle by forming the exit surface 220 of the prism 200 in the shape of a concave spherical surface or a convex spherical surface, as illustrated in FIGS. 3 and 4, other than adjusting the angle of the prism 200.

In the drawings, the lighting angle-P is a lighting angle in the case in which the exit surface 220 of the prism 200 is a plane, the lighting angle-S is a lighting angle in the case in which the exit surface 220 of the prism 200 is a convex spherical surface, and thus the lighting angle is made narrow, and the lighting angle-E corresponds to the case in which the exit surface of the prism 200 is formed in the shape of a concave spherical surface and thus the lighting angle is made wide.

The core gist of the present invention is that the lens for iris recognition 10 is provided, the prism 200 is disposed in the upper portion of the guide 30 to cover the lighting IR LED 20 with the lighting IR LED 20 near and beside the lens 10 vertically installed in the guide 30 and the prism 200 is configured such that the bottom surface thereof is configured as the inclined incident surface 210 and the top surface thereof is configured as the planar exit surface 220, thereby enabling the iris to be recognized over a short distance, preferably within a range of 3 to 20 cm.

In addition, the minute protrusions 230 are formed on the incident and exit surfaces 210 and 220 of the prism 200 by etching, and thus the light of the lighting IR LED is scattered, thereby making brightness uniform.

The angle of the prism is determined in compliance with Snell's law (the law of refraction).

That is, if it is assumed that the incident angle is i, the refraction angle is r, the refractive index of a receptive medium is v1, and the refractive index of a refractive medium is v2, the value of sin(i)/sin(r) is the refractive index that is given when light travels from vacuum to a specific material.

That is sin(i)/sin(r)=v1/v2.

Figure 11:
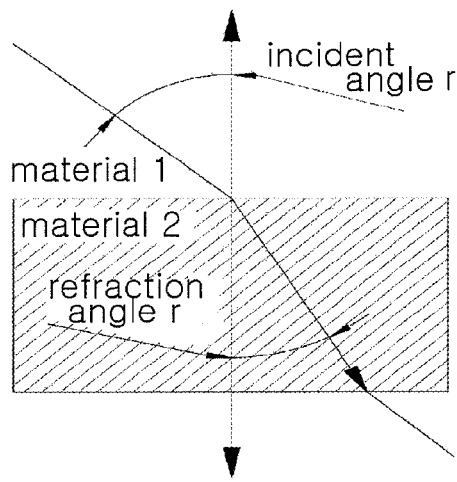
FIG. 11 is a diagram showing the relationships between incident and refraction angles so as to illustrate the present invention.

When this is represented using a diagram, FIG. 11 is obtained.

When light travels from vacuum to a specific material, v1 is 1. When light travels from air to a specific material, v1 is commonly 1.

A material that is used to refract illumination light is inexpensive, and can be easily obtained. As the material, acryl having an excellent transmittance of about 90% or PMMA (polymethyl methacrylate) may be used, or another transparent material, such as polycarbonate, may be used.

The refractive index of the PMMA material is estimated to be about 1.494 in the green light region (546 nm), and to be about 1.48 as an average value in the infrared region (750 to 900 nm).

A schematic formula that obtains the angle of the prism 200 may be established as follows.

When the distance from the lens center line I/C of the lens 10 to the lighting center line I/C of the lighting source 20 is D, and the distance from an end of the lens 10 to an eye is L, and the lighting IR LED (lighting source) 20 is vertically erected, the angle of the prism 200 becomes the same as the incident angle of the lighting IR LED 20, and the angle LA between the lighting center line I/C and the lens center line L/C of the lens 10 is arctangent D/L.

The present invention enables the lighting IR LED (lighting source) 20 to be relatively easily installed because it can be vertically installed using a simple assembly jig, and enables manufacturing quality to be easily maintained because it is easy to determine whether the lighting IR LED (lighting source) 20 has been vertically installed.

Furthermore, the present invention is not susceptible to erroneous operation because it is resistant to external static electricity, and it consumes only a small amount of power to achieve the same amount of light.

In another application, the angle between the lens center line L/C and the lighting center line I/C can be easily adjusted and applied by adjusting only the angle of the prism 200.

To perform iris recognition, a user should place his or her iris exactly on the object plane of the lens 10. For this purpose, a user is notified that the camera is in focus via voice guidance or the like by using a program that measures the definition of images, thereby providing guidance so that the user's iris is located exactly on the object plane of the lens 10 of the camera.

However, since the threshold value for the measurement of definition varies depending on the number of patterns of the iris, there are cases in which recognition fails (the number of iris patterns is large) because actually an iris image is not clear even when an indication of being in focus is given.

In contrast, since there are cases in which recognition fails (the number of iris patterns is small) because an indication of being out of focus is given even when an iris is image is clear, is problematic to determine and use a threshold value for the definition of an iris image.

In the present invention, to enable a user to place his or her iris exactly on the object plane of the lens 10, primary guidance is provided using the circular or rectangular mirror 310 formed of an elliptical mirror, and then secondary guidance is provided to perform capturing at an accurate location by visually or aurally providing notification that iris recognition is being performed via a sound device or an indication light 300 to a user using a program that determines whether iris recognition can be performed on an image, thereby significantly increasing the success rate of iris recognition.

The circular or rectangular elliptical mirror 310 is installed above the lens 10.

That is, the present invention provides visual or aural notification to the user when the iris is recognized after the definition of the iris and the focus have been met, unlike in the conventional method that determines whether the iris has been recognized based on the focus, regardless of the definition of the iris.

Mode For Invention

Figure 6:
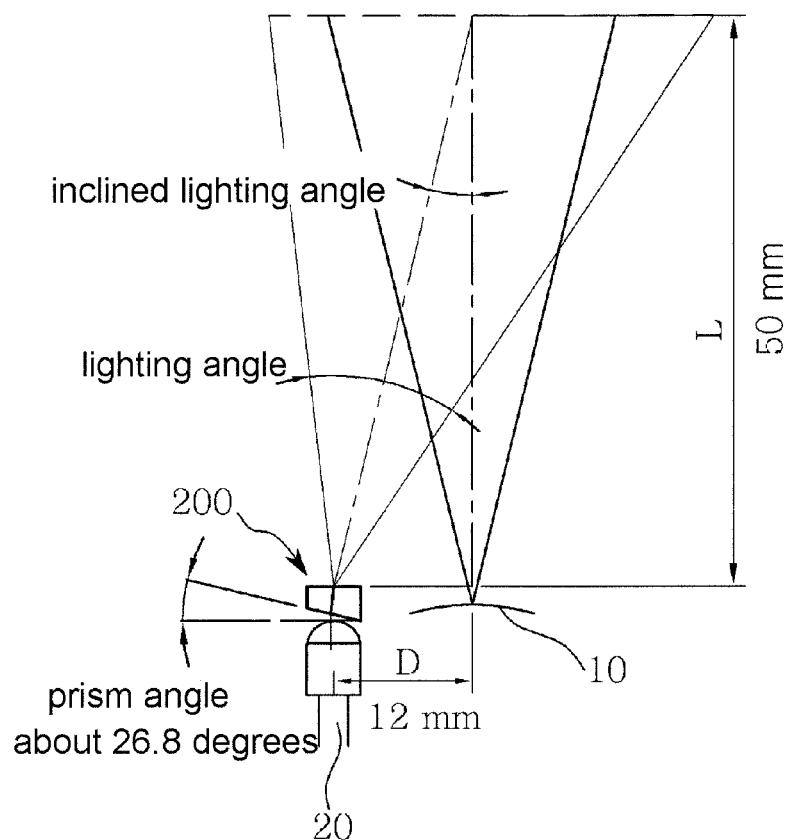
FIG. 6 is a diagram illustrating the acquisition of prism angle.
Figure 7:
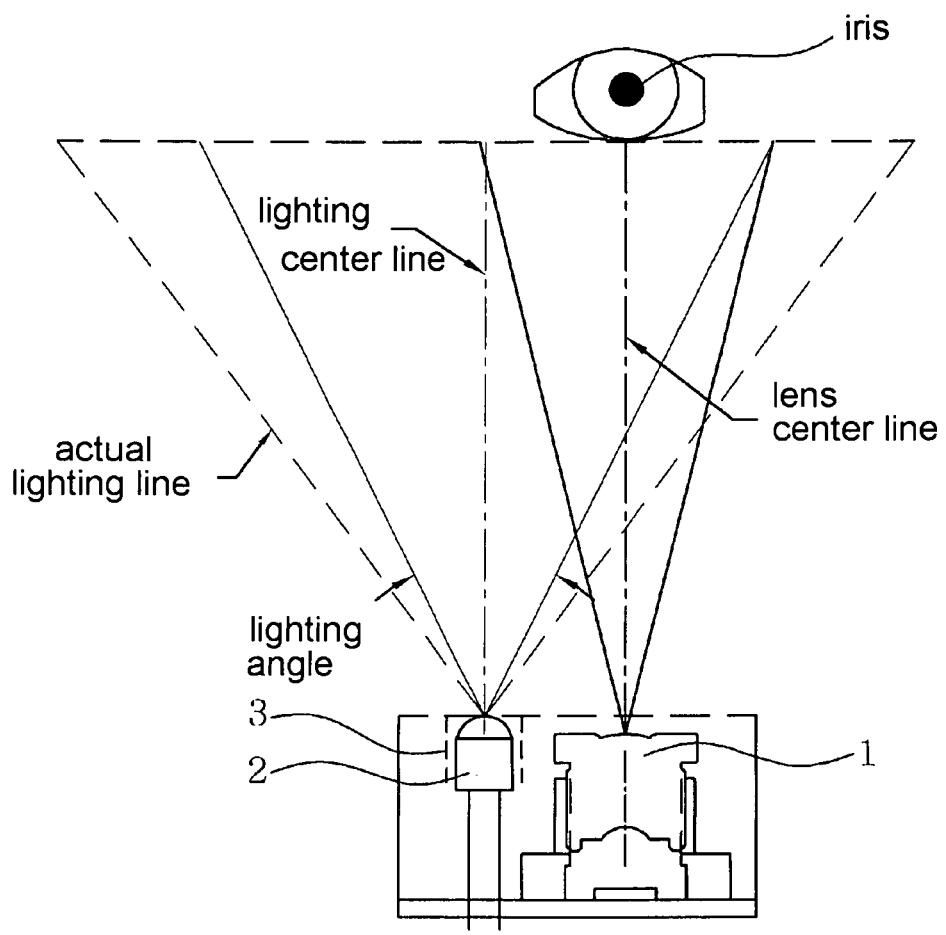
FIG. 7 is a schematic plan view illustrating a lighting angle when a conventional lighting IR LED is used.
Figure 8:
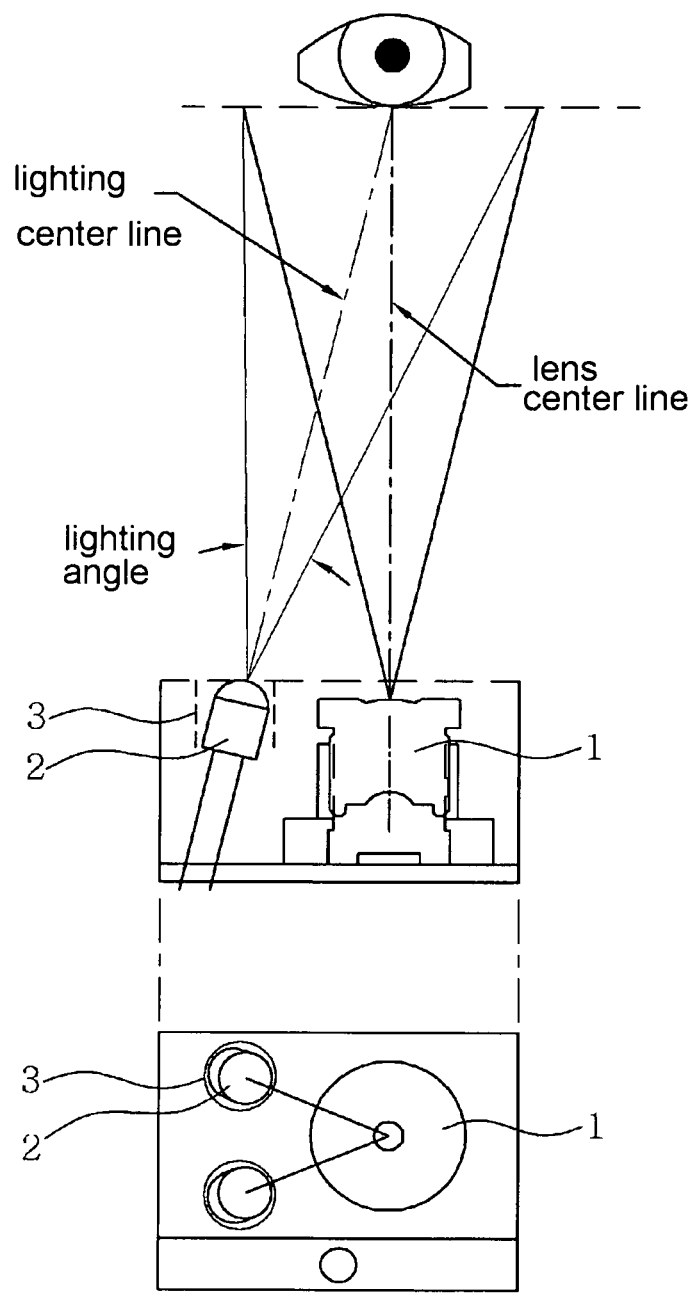
FIG. 8 shows schematic plan and front views illustrating a lighting angle when the lighting IR LED of FIG. 7 is inclined.
Figure 9:
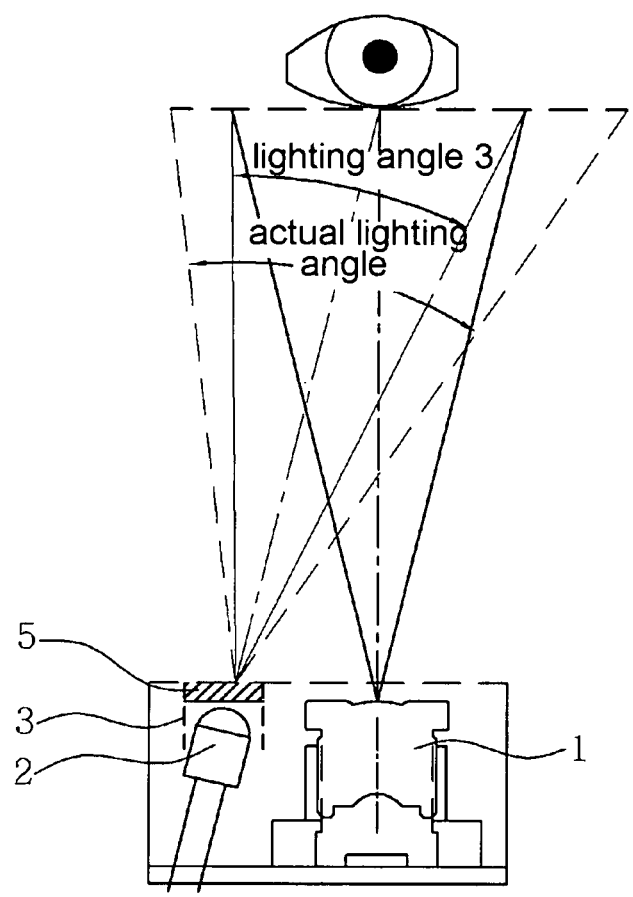
FIG. 9 is a schematic plan view illustrating a lighting angle when the lighting IR LED of FIG. 8 is covered with a planar prism.
Figure 10:
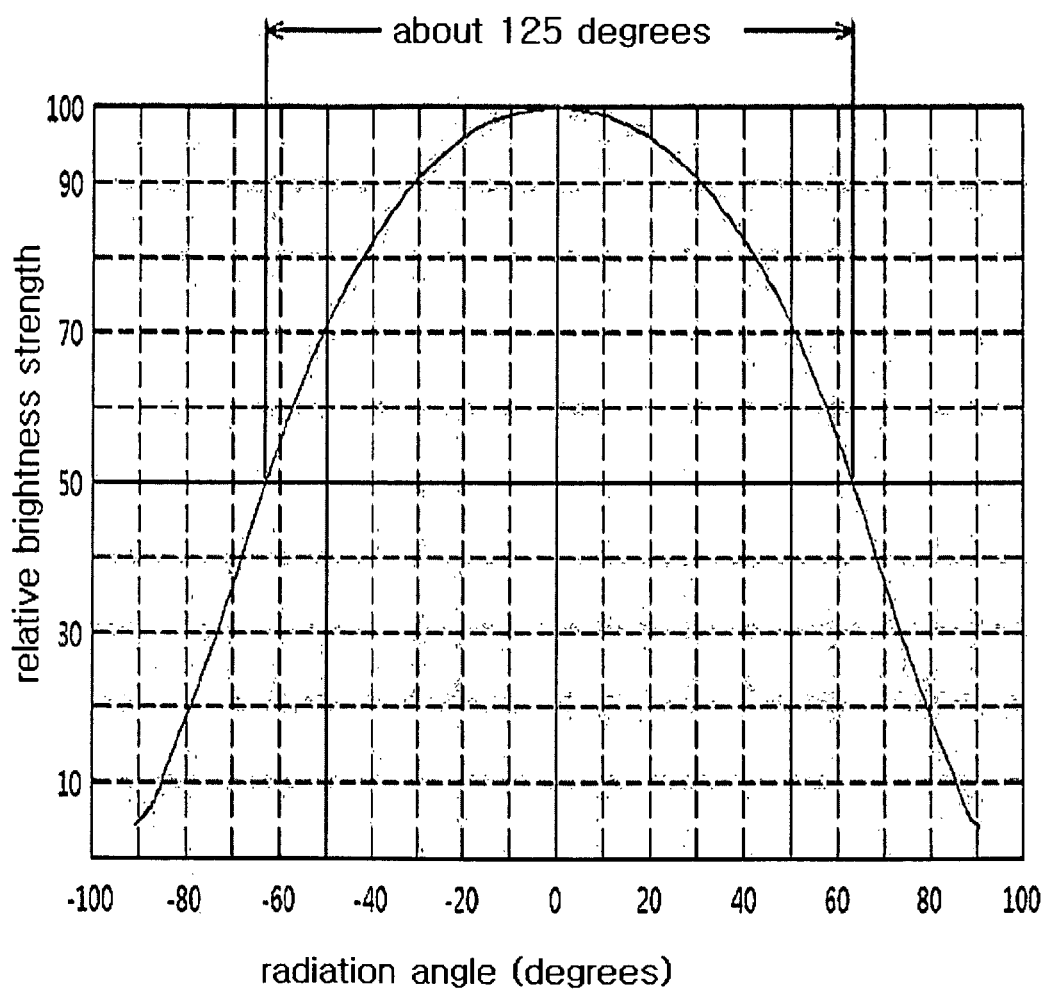
FIG. 10 is a graph illustrating an example of the radiation angle of a lighting IR LED.

When a lighting IR LED 20 is vertically disposed, the range of lighting wavelengths spans from 750 to 900 nm, the distance 13 from the center of a lens 10 to the center line I/C of illumination light is 12 mm, the distance L from an end of the lens 10 to an eye is 50 mm, and the refractive index of a PMMA material is set to 1.48, as illustrated in FIG. 6, the angle LA of a prism is about 26.8 degrees in accordance with the above-described law of refraction.

To achieve resistance against static electricity, an iris capturing camera module is made of a plastic material, such as ABS or polycarbonate, a prism is formed to have a thickness of about 3 mm, and PMMA is used as the material of the prism. In this case, the dielectric breakdown strength reaches 15,000~20,000 volt per mm. As a result, insulation against external static electricity of 4 to 8 thousands of volts can be achieved, and thus erroneous operation is prevented.

Furthermore, the uniformity of brightness on an object plane on which an eye is located can be considerably improved by forming minute protrusions on incident and exit surfaces.

In addition, the disposition and density of minute protrusions may be adjusted in accordance with desired uniformity and a desired lighting angle.

As in the conventional method, due to the low uniformity of brightness, there is a strong probability of an error occurring in the processing of a program that is performed to find feature points from an image, such as an image of a blue or gray eye, that has low contrast in itself. This will be fully understood by those skilled in the art even when it is not described in this specification.

In the conventional case and the example of the present invention, the uniformities of light are compared with each other based on "brightness_maximum value/brightness_minimum value," and a result that has been improved twice can be obtained.

Figure 12:
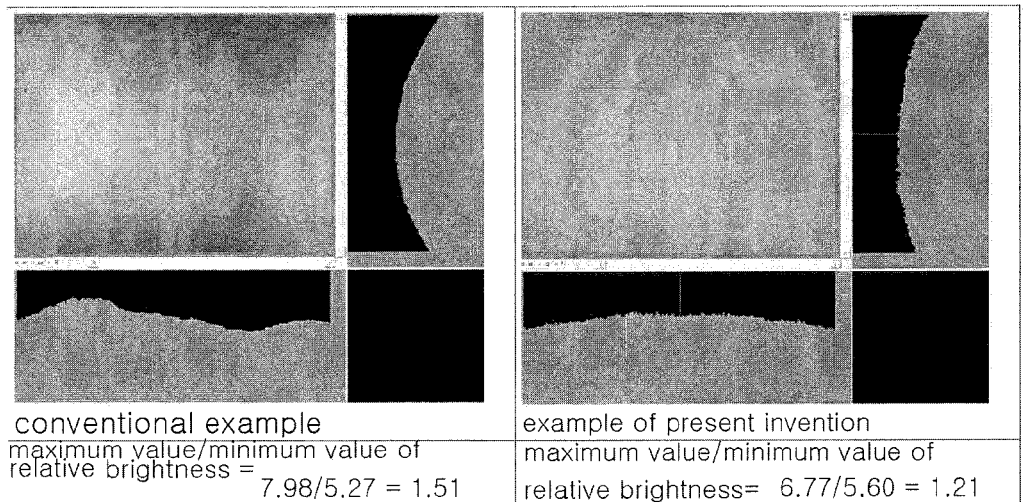
FIG. 12 shows photos illustrating the comparison between the uniformities of brightness according to the method of the embodiment of the present invention.

An example, according to the method of the embodiment, in which the uniformity of light has been improved is shown in the comparative photos of FIG. 12.

INDUSTRIAL APPLICABILITY

The present invention can be used in a short distance iris recognition camera so as to improve the uniformity of brightness around the iris without changing the state of a lighting IR LED being installed and to prevent static electricity from being discharged to internal circuits.

The invention claimed is:

1. A short distance iris recognition camera comprising:
a sensor and appendant circuits,
a lens,
a lighting source including a white light source and a lighting IR LED, and
a prism, and
wherein the lighting source is spaced apart from a lens center line of the lens in a first direction by a first predetermined distance D,
wherein an object plane of the lens is a location at which an iris is placed, is spaced apart from an end of the lens in a second direction orthogonal to the first direction by a second predetermined distance L, and occupies a region around the lens center line,
wherein an imaging surface of the lens is an image sensor surface, and
wherein a lighting center line is formed to have an inclined lighting angle corresponding to an arc tangent of said first predetermined distance D to said second predetermining distance L with the lens center line of the lens to be oriented to the object plane of the lens,
wherein the lighting source is disposed to have an orientation in parallel with or approximately in parallel with the lens center line of the lens, and
wherein the prism is disposed to be spaced apart from the lens center line of the lens in a light path of the lighting source and to irradiate the object plane in an inclined manner so as to give said lighting center line of light from the lighting source said inclined lighting angle.

2. The short distance iris recognition camera of claim 1, wherein primary guidance is provided using a mirror formed of an elliptical mirror so that the iris is placed exactly on the object plane of the lens, and a sound device or indication light that provides notification that iris recognition is being performed is used to provide secondary precise guidance.

3. The short distance iris recognition camera of claim 1, wherein an incident surface of the prism is configured as an inclined surface so as to irradiate the object plane with respect to the vertical disposition of the lighting IR LED.

4. The short distance iris recognition camera of claim 1 or 3, wherein minute protrusions are formed on both or one of incident and exit surfaces of the prism to disperse light and thus make brightness uniform.

5. The short distance iris recognition camera of claim 1 or 3, wherein the exit surface of the prism is configured as a convex spherical surface or a concave spherical surface, thereby adjusting lighting to an arbitrary angle.

6. The short distance iris recognition camera of claim 1, wherein the lighting IR LED includes a guide, and wherein the prism is disposed at an upper side of the guide to cover the lighting IR LED so as to receive all light emitted from the lighting IR LED.

7. The short distance iris recognition camera of claim 1, further comprising a casing, and wherein the prism and the lens each have a respective exit surface on a same plane as a top surface of the casing.

* * * * *